United States Patent [19]
Wong

[11] Patent Number: 5,498,158
[45] Date of Patent: Mar. 12, 1996

[54] COLOR-CODED ENDODONTIC CUTTING INSTRUMENTS AND COLOR-CODE SYSTEM AND METHOD

[76] Inventor: Nelson J. Wong, 2101 Midway Rd., Suite 250, Richardson, Tex. 75006

[21] Appl. No.: 197,644

[22] Filed: Feb. 14, 1994

[51] Int. Cl.$^6$ ..................................................... A61C 5/02
[52] U.S. Cl. ....................................................... 433/102
[58] Field of Search ................................. 433/102, 141, 433/143, 147, 224; 16/110 R, DIG. 12, DIG. 18, DIG. 19; 81/177.1, 489; 40/913

[56] References Cited

U.S. PATENT DOCUMENTS

| | | | |
|---|---|---|---|
| 3,935,640 | 2/1976 | Cohan. | |
| 4,117,791 | 10/1978 | Current et al. | 112/222 |
| 4,158,746 | 6/1979 | Taylor et al. | 174/112 |
| 4,169,173 | 9/1979 | Bergholm et al. | 427/284 |
| 4,253,830 | 3/1981 | Kazen et al. | 433/77 |
| 4,332,561 | 6/1982 | McSpadden | 433/102 |
| 4,340,364 | 7/1982 | Deemer | 433/75 |
| 4,385,281 | 5/1983 | McAlear et al. | 337/186 |
| 4,559,936 | 12/1985 | Hill | 128/92 R |
| 4,649,678 | 3/1987 | Lamson | 52/103 |
| 4,674,979 | 6/1987 | Jacklich | 433/102 |
| 4,841,653 | 6/1989 | Negley | 40/625 |
| 4,850,874 | 7/1989 | Weissman | 433/225 |
| 4,859,183 | 8/1989 | Martin | 433/102 |
| 4,889,487 | 12/1989 | Lovaas | 433/102 |
| 4,934,934 | 6/1990 | Arpaio, Jr. et al. | 433/102 |
| 4,936,170 | 6/1990 | Zumeta | 81/180.1 |
| 4,982,627 | 1/1991 | Johnson | 81/121.1 |
| 5,017,138 | 5/1991 | Schilder | 433/102 |
| 5,031,488 | 7/1991 | Zumeta | 81/180.1 |
| 5,083,921 | 1/1992 | Dragan | 433/90 |
| 5,104,322 | 4/1992 | You | 433/224 |
| 5,182,895 | 2/1993 | Lugo | 53/469 |
| 5,251,751 | 11/1993 | Prussen | 206/338 |
| 5,289,919 | 3/1994 | Fischer | 433/77 |

OTHER PUBLICATIONS

Clyde L. Sabala, D.D.S., and John T. Biggs, D.D.S., MEd, "A Standard Predetermined Endodontic Preparation Concept," Compend Contin Educ Dent, vol. XII, No. 9, pp. 656, 658, 660, 662, 663.

Michael A. Heuer and Leo J. Miserendino, "Instruments and Materials," *The Science of Endodontics*, pp. 397–410.

J. J. Messing and C. J. R. Stock, *Color Atlas of Endodontics*, "Fractured Instruments—Prevention and Retrieval" (6 pages).

Louis I. Grossman, D.D.D., Seymour Oliet, D.D.S., and Carlos E. Del Rio, D.D.C., *Endodontic Practice*, "Preparation of the Root Canal: Equipment and Technique for Cleaning, Shaping and Irrigation." Philadelphia (1988), pp. 192–210, 212–213, 216–222.

Franklin S. Weine, *Endodontic Therapy*, 2nd Ed. Saint Louis: The C. V. Mosby Company, 1976), pp. 70, 120–123, 152–155, 160–163, 206–207, 214–223, and 242–243.

Ad: "Introducing ProFile™ Series 29—A Sizeable Improvement In Endodontic Files." Tulsa Dental Products, Tulsa, Oklahoma (brochure).

(List continued on next page.)

*Primary Examiner*—Cary E. O'Connor
*Attorney, Agent, or Firm*—John W. Montgomery; Ross, Clapp, Korn & Montgomery

[57] ABSTRACT

A set of endodontic cutting instruments, each having handles and each having a different working tip diameter incrementally increasing in size from one instrument to the next. The set includes a first smaller standard size endodontic cutting instrument having a grasping end with a first color according to a standard color code, a second larger standard size endodontic cutting instrument having a grasping end with a second color according to the standard color code and a non-standard intermediate size endodontic instrument having a size between the first smaller standard size and the second larger standard size and having a grasping end with a color combination including a first portion having the first standard color corresponding to the first smaller standard size and a second portion having the second standard color corresponding to the second larger standard size.

26 Claims, 8 Drawing Sheets

OTHER PUBLICATIONS

Ad: "ProFile™ Series 29 Standards," and 2 pages of order forms—Tulsa Dental Products, Tulsa, Oklahoma.

Ad: "1993's Hottest Tips for Endodontic Success—ISO Files, ProFile™." Tulsa Dental Products, Tulsa, Oklahoma.

Ad: "The Comb, According to ISO File Standards—The Comb, According to ProFile Series 29 Standards. Profile, distributed by Tulsa Dental Products, The Makers of Thermafil."Ad: "Brasseler Canal Master 'U'™—A New Expanded Line of Canal Master Instruments." (5 pages).

Ad: "From the Kerr Team—Endodontic Expertise . . . in your hands." Kerr/Division of Sybron Corporation, Romulus, Michigan.

Ad: "Advances in Dentistry—Designed with the gloved hand in mind—MAXI-CON™ Grips." Block Drug Corp., Jersey City, NJ.

Ad: "The Better Dental Alternative—Ti-Flex Nickel Titanium Endodontic Files." DDW (1-800-336-8486).

Ad: "protect yourself by using Mynol Endodontic instruments with preinserted rubber stops." Block Drug Co., Jersey City, NJ.

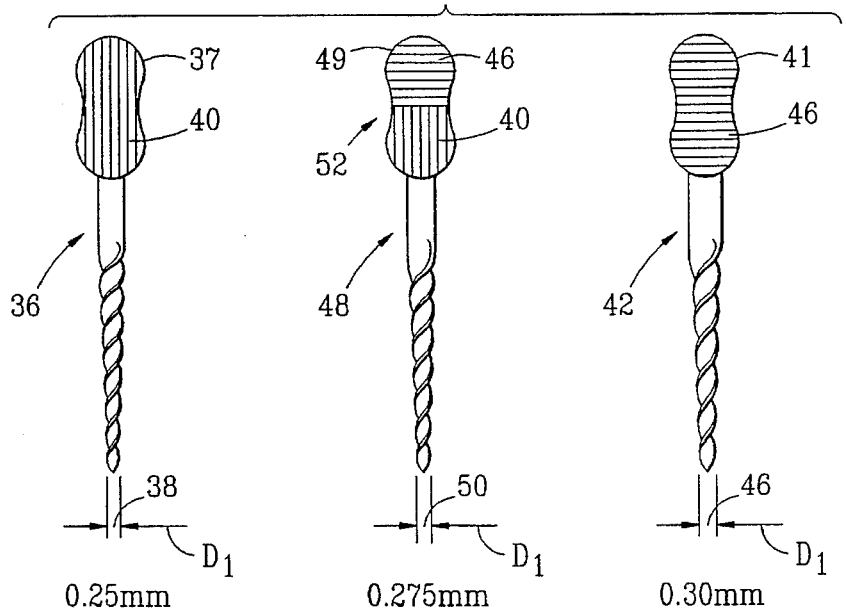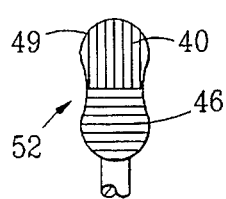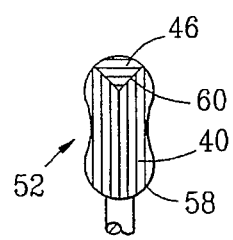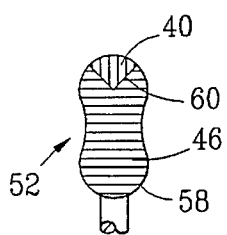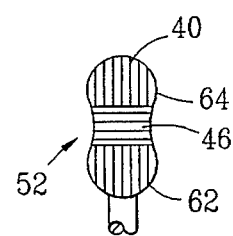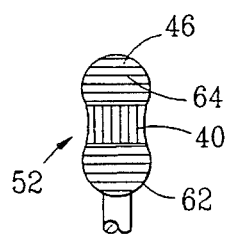

5,498,158

COLOR-CODED ENDODONTIC CUTTING INSTRUMENTS AND COLOR-CODE SYSTEM AND METHOD

TECHNICAL FIELD OF THE INVENTION

The present invention relates to improved endodontic cutting instruments and, in particular, to improved sets of color-coded endodontic files or reamers and to a system by which a dentist recognizes the size differences in standard size instruments and intermediate, non-standard size instruments.

BACKGROUND OF THE INVENTION

Endodontics, also known loosely as root canal therapy (RC) is a major part of dental treatment especially where saving an infected tooth is concerned. Endodontic instruments used to negotiate the canals inside the roots of teeth consist primarily of files and reamers. These instruments may be machine-driven, in which case a grasping end or shank is firmly grasped in a machine collet or chuck, such as in a rotary drill, a reciprocating filing machine or in an ultrasonic vibrating machine. Because of the sensitive nature of the root canal procedure and the small sizes of the cutting instruments, hand-held files and reamers are popular. Typically, hand-held files and reamers are provided with miniature or finger-size handles as a grasping end by which the dentist grasps the non-working end of the instrument for manipulation within the tooth nerve canal.

Files are elongated, round endodontic instruments designed for removing dentin from the inside of a tooth primarily with a vertical movement in the axial or elongated direction. Reamers are similarly elongated, rounded endodontic cutting instruments; however, they are designed primarily for enlarging or smoothing a hole in a tooth by the removal of dentin from the inside of the tooth primarily through rotation. Because of the difference in operation (i.e., an up-and-down movement, compared with rotational movement), files typically have a greater number of cutting edges and a higher twist angle and reamers have fewer cutting edges and a lower twist angle. Under the ISO standards, a file typically has four cutting edges formed as by twisting a small shaft having a square cross-section such that each of the four corner forms a cutting edge. The flat faces of the square form clearance flutes. A reamer is typically formed by twisting a triangular cross-sectional-shaped shaft such that it has three edges. The flat faces of the triangle form clearance flutes. The high twist angle of the files provides the cutting edge with a significant horizontal component relative to the up-and-down movement. The low angle of twist on a reamer provides the cutting edge with a significant vertical component for cutting by rotational movement. Many manufacturers have presented differently shaped cutting edges and flutes in order to provide different cutting characteristics.

U.S. Pat. No. 5,017,138 has, in its Background of the Invention, a summary of how endodontic instruments are standardized through the International Standard Organization (ISO). Basically, the shape, length, size and handle color of endodontic instruments are defined by ISO's Standard 3630. FIG. 1 shows a prior art endodontic cutting instruments basically according to the current ISO standards.

Pursuant to Standard 3630, the diameter of the working tip of an endodontic file (or reamer) corresponds to the number that is used to identify the file. For instance, an ISO standard size 10 means that the working tip diameter, so called "$D_1$" (as opposed to "$D_2$" which is the shank diameter further up the file), measures 0.10 mm. The next larger standard size file would be No. 15, indicating a working tip diameter of 0.15 mm at $D_1$. The next larger standard size is 20, then 25, then 30, then 35 and so on, indicating 0.05 mm incremental size changes from one standard size to the next larger standard size until size 60 is reached. After size 60, then diameters at $D_1$ increase by 0.1 mm for each standard size increment so that the next standard size file greater than size 60 is size 70 with a diameter $D_1$ of 0.75 mm. Then, 80, 90, 100 and so on every 0.10 mm until size 150. However, apparently the largest size commonly available on the market is 140.

Other than the standardization of the working tip diameters and the standardization of incremental size difference between each diameter, the other noteworthy feature about the ISO standard is that it establishes an accepted international standard color scheme for the endodontic file and reamer handles. These colors are fixed and then correspond to the size of the tip diameter. Six basic colors are used, and accordingly to the ISO scheme, are repeated. The colors are: white, yellow, red, blue, green and black. Files outside of the standard range are sometimes available from various manufacturers, but there has been no accepted standard color scheme for differentiating the non-standard sizes from the standardized sizes. Some manufacturers have developed their own unique colors, and some have merely printed different size measurements on the handles. Confusion has not been avoided.

Dentists and dental assistants can still depend on the fact that an ISO size 15 file will be white in color. This is also the file that most root canals are started with. When the dentist begins to negotiate the length of the root canal completely and reach the root tip with a size 15 file or reamer without blockage or binding, the next larger file, size 20 (which is yellow in color) is grasped or handed to the dentist by an assistant for removing additional material until the tip is reached. The process is repeated, step-wise, with the next larger size 25 (which is red). Then, the size 30 (which is blue), the size 35 (which is green) and followed by size 40 (which is black). The size differences and color-coding are set forth in Table I, below.

TABLE I

ISO STANDARD COLOR CODE SYSTEM

| | Diameter of Instrument | | |
|---|---|---|---|
| Size | $D_1$ (mm) | $D_2$ (mm) | Color |
| 10 | 0.10 | 0.42 | Purple |
| 15 | 0.15 | 0.47 | White |
| 20 | 0.20 | 0.52 | Yellow |
| 25 | 0.25 | 0.57 | Red |
| 30 | 0.30 | 0.62 | Blue |
| 35 | 0.35 | 0.67 | Green |
| 40 | 0.40 | 0.72 | Black |
| 45 | 0.45 | 0.77 | White |
| 50 | 0.50 | 0.82 | Yellow |
| 55 | 0.55 | 0.87 | Red |
| 60 | 0.60 | 0.92 | Blue |
| 70 | 0.70 | 1.02 | Green |
| 80 | 0.80 | 1.12 | Black |
| 90 | 0.90 | 1.22 | White |
| 100 | 1.00 | 1.32 | Yellow |
| 110 | 1.10 | 1.42 | Red |
| 120 | 1.20 | 1.52 | Blue |
| 130 | 1.30 | 1.62 | Green |
| 140 | 1.40 | 1.72 | Black |
| 150 | 1.50 | 1.82 | White |

The six colors are repeated again after size 40 (which is black) with ISO standard size 45 being white again. The standard size 50 is yellow, size 55 is red and size 60 is blue. As stated above, from standard size 15 to standard size 60, the standard incremental increase in working diameter is 0.05 mm. From size 60 to size 150, the standard incremental working diameter increase is 0.10 mm. The standard color scheme repeats sequentially for each next larger standard size. Since there is no standard size 65, size 70 is the next color in the sequence (i.e., green), size 80 is black. Size 90 initiates the repetition of the sequence at white; then size 100 is yellow, size 110 is red, size 120 is blue, size 130 is green, through size 140 which is black. Size 150 is white, but is seldom used and is seldom commercially available. From size 15 to size 140, there are eighteen different standard endodontic instrument sizes for files and reamers under the ISO system. The color scheme of white-yellow-red-blue-green-black repeats three times.

If the dentist encounters a problem negotiating the root canal with a size 15 instrument, there are now three smaller ISO-recognized standard sizes—10, 8 and 6— with corresponding working tip diameters of 0.1 mm, 0.08 mm and the very fine 0.06 mm. They bear special ISO colors of purple, silver and pink, respectively.

This color scheme is taught to dental students from the beginning of their studies in endodontics. By the time the student graduates from dental school, he or she invariably has become very familiar with the scheme for standard sizes. If a white file is encountered, he or she immediately recognizes it as either a size 15, 45 or 90. A very large ISO file would be obvious. The size difference from one standard whole size to the next (i.e., 0.05 mm or 0.10 mm increase) can be difficult to distinguish by mere visual observation without a color code. With six standard whole sizes between each repeated color, there is a sufficient size variation for most dentists and trained personnel to distinguish between each of the files of the same color even if the complete set of files becomes mixed as on a tray out of sequence.

Manufacturers of endodontic files typically color code and number their files and reamers on the handles. However, during an endodontic procedure, observation of small printed numbers is frequently obscured by materials or the dentist's fingers. It is noted that the file handles are typically only about 1 cm in length and about 0.5 cm in diameter. It is also noteworthy that the standardization of incremental increases from one whole size to the next for endodontic instruments by 0.05 mm for sizes 15 to 60 and by 0.10 mm for sizes 60 to 140 is a collective effort on the part of manufacturers and practitioners in the art. As with most well-meaning efforts, some controversy and problems have arisen. The 0.05 mm incremental increase, in some cases, has been too much. That is, sometimes where a canal can comfortably be negotiated by one standard size, it will not allow the negotiable by the next larger size which is at least 0.05 mm larger for each standard incremental size.

Recognition of this problem is not new. In the seminal book, *Endodontic Practice* (11th Ed.), by Grossman, et al., the authors discuss a hypothetical, yet commonly encountered, situation. In the scenario offered by the textbook, a size 10 file will go the distance of the canal but a size 15 file will not. The authors suggest that, "[b]ecause the next size file needed is not available commercially, the operator can create one by cutting off part of the instrument tip of the size 10 file. All standardized instruments taper 0.02 mm in diameter per 1.0 mm of blade length. Cutting off 1.0 mm of tip of a size 10 file converts it to a size 12 file." (p. 208) Of course, the resulting working tip, which was originally at a 75° angle per ISO standards, may cut unevenly unless great skill and care is exercised to recreate a symmetrically-angled cutting tip.

More than one Endodontic textbook as well as numerous dental seminars have taught the above-mentioned method of creating "intermediate" files to the ISO system. The problem of not being able to go the distance with the next larger file has also created the problem of broken files: As the next larger file is just a little short of the length of the canal, it is not uncommon for the operator to push a little harder. The file then binds and in an attempt to pull the file out, it breaks. This has led to the oft-quoted rule in endodontics of "No more than one quarter turn" in using files and reamers.

As a result of the foregoing, many dental articles have been written about how to retrieve broken files as well as implements for sale to dentist to do same. This is also the backdrop of the U.S. Pat. No. 5,017,138.

The '138 patent criticizes the ISO's system of fixed 0.05 my incremental increase as providing a non-uniform percentage increase in size over the 0.1 mm to 1.4 mm range. The proposed solution is to offer uniform percentage increases in files rather than a fixed amount of increase. Under the proposed '138 uniform percentage increase scheme, each subsequent file would increase the same percentage in size as oppose to an irregular percentage under the ISO system.

The 0.05 mm incremental increase under the ISO mathematically does have an irregular percentage increase in file size. For instance: from size 10 to size 15, that is from 0.10 to 0.15, a 0.05 mm increase equates a 50% increase. From 15 to size 20, that is from 0.15 to 0.20, a 0.05 increase equals a 33% increase. This irregular, albeit decreasing percentage, was pointed out in the '138 patent. However, where the '138 patent fails is that even in a thirteen-instrument set (the widest selection in the examples given), for a uniform increase of 29%, after the tip size reaches 0.167 mm (instrument 5), the size increase up to the next size of 0.216 mm (instrument 6) is 0.049 mm [column 4, line 6 of the '138 patent]. We are essentially back to the ISO increase of 0.5 mm.

Above Instrument 6, the 29% increase translates to a whopping 0.063 mm between size (instruments 6 and 7): 0.216 mm and 0.297 mm [column 4, line 7]. Then a gargantuan leap of 0.087 mm. between sizes 0.297 mm and 0.366 mm (instruments 7 and 8). By the time instrument 13 is reached with a $D_1$ of 1.293 mm. (similar to an ISO size 130 file), there is a giant 0.293 mm increase over instrument 12 [column 4, line 54]. This is three times the 0.10 mm increase under the ISO system!

Another important disadvantage of the '138 system is that it involves a totally different color scheme. At this writing, one manufacturer has offered for sale a series of 13 files based on the '138 patent. The manufacturer used its own color code in which four colors are repeated twice plus five other colors for the set of thirteen instruments. These nine new colors include several hues of brown and green. There are also two different reds, plus a pink.

It is reasonable to think that the manufacturer of the '138 set of files is trying hard to prevent any overlap of colors with the ISO colors. Imagine the dentist (or, more likely, the chairside assistant) haplessly trying to find the next larger size with file colors closely resembling one another. However, in creating new colors, the manufacturer also has unwittingly forced the user of these new files to memorize a new set of colors. Habits are hard to form and even harder to forget.

The problem with the 0.05 mm. increase under the ISO system is also drawing the attention of another manufacturer. Recently, a new set of endodontic files has been introduced which are the "half-sizes". No longer do dentists have to bring along a fingernail file in their endodontic boxes to clip file tips in order to make custom intermediate sizes. New non-standard half-sizes of 22.5, 27.5, 32.5, 42.5, and 47.5 corresponding to 0.225 mm, 0.275 mm, 0.325 mm, 0.425 mm and 0.475 mm tip diameters have been introduced. However, this only addresses part of the problem.

The problem relating to the identification of half-sizes has not been adequately addressed. These non-standard size files are in-between existing standard sizes or intermediate sizes and need to be identified properly in order that the user can quickly select the appropriate one during the root canal procedure. As with the '138 file set, a totally different color scheme will be confusing at best and will likely never be adopted or relearned. The mere printing of sizes on the small handles is inadequate in a realistic situation. More than one intermediate size in critical working ranges has not been previously proposed.

SUMMARY OF THE INVENTION

The present invention relates to an improved set of endodontic instruments by a method of representing or identifying files or reamers that are intermediate of the ISO standard sizes. This invention also offers representative file systems based upon the embodiments of this disclosure.

The present invention recognizes that the current ISO coloring system is what dentist, dental students and root canal specialists have been accustomed to. It is not likely that a system of new colors would work due largely to inertia and the formidable task of remembering multiple new colors. This is similar to the inertia and aversion one has in converting to the metric system. Unless legislated to do so, it is unlikely a voluntary conversion would take place.

While the intermediate size files solve some of the problems of ISO's infamous 0.05 mm. incremental increase and would no doubt reduce the breakage of files inside canals and drastically improve the lives of RC operators, the method of identifying these now "new" files have yet to be offered. This invention fills the void and presents the solution to aid the operator to quickly identify an intermediate size.

It is one object of this invention to provide a system by which an intermediate file can be identified by providing a combination of standard ISO colors on non-standard intermediate size files. The size could be visually determined using only the same colors currently used in the ISO standard system. Files and reamers having a size intermediate to existing standard sizes are uniquely provided with grasping ends or handles having a combination of a standard color corresponding to the next smaller size and of a standard color corresponding to the next larger standard size. Any other non-standard size which falls between two standard ISO sizes could be identified, with the next smaller and next larger color combination, including even those sizes which are not exactly halfway between two ISO sizes. A set of files, including intermediate size files, with sizes which are exactly midway between the next smaller and next larger standard ISO file sizes would be a logical embodiment. Half of the marking area on the grasping end, whether on the shank or on the handle, would be one ISO standard color, and the other half of the marking area would be a color representing the next larger standard size. However, that is not the only possible embodiment. For example, an RC operator may not be very concerned where in the 0.05 mm differential range the mid-size file falls, only that the file is somewhere in between. According to the '138 patent, files could be identified according to their size, relative to the standard ISO file sizes. Confusion could be greatly reduced.

According to another object of this invention, an intermediate size file that is closer in size to one ISO file size could be identified and distinguished from another intermediate size file closer in size to the next larger file. Applying the disclosure herein, one could identify a file—for example, the equivalent to an ISO size 63.3 (remember that there is no ISO size 65 file), as well as a file equivalent to an ISO size 66.7—without using any new colors. According to one embodiment, a percentage color coverage could be used to show a relative size relationship. According to another embodiment, a number of colored shapes or rings could indicate small intermediate increments by which a size relationship would be identified. According to another embodiment, the position of colored shapes or rings relative to one end of a handle could indicate relative size within the intermediate range between one ISO size and the next larger size.

It is another object of the invention to provide a method by which originally standard size files which are converted to non-standard sizes could be marked after conversion by applying a color to the converted instrument so that a color combination is formed according to the invention.

BRIEF DESCRIPTION OF THE DRAWINGS

These and other objects and advantages will be more fully understood with reference to the following specification, claims and drawings in which like numerals represent like elements and in which:

FIG. 2a is a schematic depiction of a set of endodontic cutting tools, depicting first and second standard size endodontic cutting tools with a non-standard, intermediate size endodontic tool therebetween and having color-coded handles according to the present invention;

FIG. 2b is an alternative embodiment of the intermediate endodontic handle of FIG. 2a in which the combination color order is reversed top to bottom;

FIG. 3a is an alternative embodiment of a color combination handle for a non-standard, intermediate size endodontic cutting tool according to the present invention;

FIG. 3b is an alternative scheme of the color combination of FIG. 3a in which the color combination is in reverse order;

FIG. 4a is an alternative scheme of the color combination of a non-standard, intermediate size endodontic cutting tool according to the present invention;

FIG. 4b is a schematic depiction of the color combination scheme of FIG. 4a in which the color combination is in reverse order;

DETAILED DESCRIPTION OF THE PREFERRED EMBODIMENTS

The ISO system of six colors repeated three times along with the three special small files have been in existence since the 1960's. It is not likely that a new coloring system would successfully replace that which is already ingrained in the minds of endodontic operators. Therefore, whosoever presents intermediate size files to the standard ISO files has to be ever so mindful of this fact.

The present invention stays within the color schemes of the ISO system, unless of course the ISO decides to change colors or even expand its system. In that case, this invention would expand and adjust to the new colors. The inventiveness continues regardless of future changes.

The most basic way to color non-standard intermediate size files for use in conjunction with the ISO system and not have to abandon years of training is to use a combination of the next smaller standard size color and the next larger standard size color.

Figure 1:
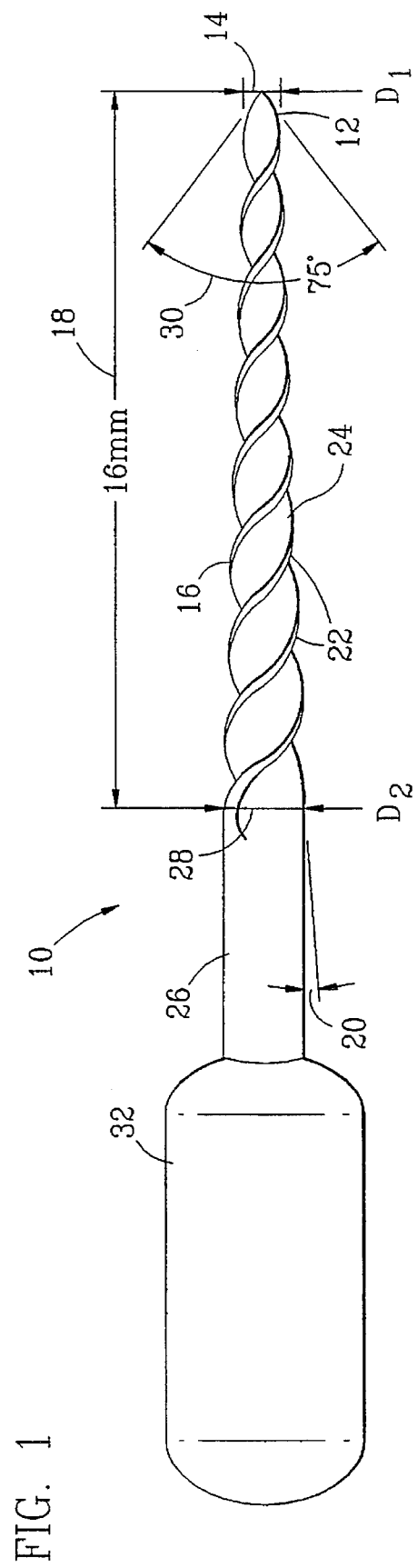
FIG. 1 is a side view of a standard prior art endodontic cutting instrument, and in particular, a standard hand-held endodontic file.

A prior art standard endodontic file is indicated in FIG. 1, which shows a side view of an enlarged endodontic file according to ISO standard terminology and dimensions. The file 10 includes a working tip 12, which has an effective working diameter or tip diameter 14 commonly designated "$D_1$". The working portion 16 of the file 10 is commonly called the "blade", and it has a standardized blade length 18 which measures 16 mm long in length. The blade 16 tapers from the tip diameter 14 at a taper angle 20, which is standard at 0.02 mm/1.0 mm, which corresponds to approximately 2°, 15'. The blade 16 is formed with cutting edges 22 and recessed flutes 24 therebetween. Typically for standard ISO files, a four-sized tapered metal wire is twisted such that there are four cutting edges 22 formed by the corners of the four-sided metal wire and four interposed flutes 24 formed by the flat faces of the four-sided metal wire. Reamers typically are formed of a triangular-shaped tapered metal wire, having three cutting edges with three interposed flutes, and are twisted at a slower rate. Thus, if the file 10 of FIG. 1 represents four cutting edges twisted two and one-half times, a reamer would typically be twisted about one and one-half times.

The taper 20 at a rate of 0.02 mm/1.0 mm, extending over the 16 mm blade length 18 expands to the shank 26 which has a diameter 28 typically designated "$D_2$". The diameter $D_2$ can be calculated for a standard length file under the ISO standard as $D_1$+0.32 mm. The working tip 12 has a standard cutting angle 30, which measures 75°±15° included angle. The entire file is provided with a handle 32 for hand operation in endodontic procedures, typically known as root canal therapy.

Set forth, above, in Table I are standard size designations 10 through 150 listed in a vertical column with corresponding columns of working diameters 14 ($D_1$) and shank diameters 28 ($D_2$). Also, in the fourth column of Table I, the standard ISO color corresponding to each size designation is listed. It will be observed that the size designation corresponds to the decimal equivalent of the working diameter $D_1$, measured in mm. It will also be noted that the standard incremental size increase of $D_1$ for each of the sizes from size 10 through size 60, is a standard incremental increase of 0.05 mm. The shank diameter $D_2$ corresponds in each case to diameter $D_1$+0.32 mm, which naturally results from a 16 mm blade length with a taper corresponding to 0.02 mm per 1 mm length.

FIG. 2a depicts a set of endodontic cutting instruments according to the present invention comprised of two selected standard size cutting instruments 36 and 42. For purposes of illustration, the smaller size instrument designated numeral 36 corresponds to standard size "25", having a working diameter 38 measuring 0.25 mm. The next larger standard size cutting instrument 42 corresponding to size "30" cutting instrument having a working diameter 49 measuring 0.30 mm. It will be understood that this particular size range selection is for purposes of demonstration only and that any adjacent pair of next smaller and next larger standard size instruments, whether file, reamer or otherwise, could be substituted in FIG. 2a according to the present invention. The instrument set of FIG. 2a further includes a non-standard, intermediate size endodontic cutting instrument 48 having a working tip diameter 50 which is a size which falls between 0.25 mm and 0.30 mm. In the particular case shown, the non-standard intermediate size file 48 is a half-size, having its working size diameter 50 equal to 0.275 mm. Each standard file 36 and 42 has a corresponding handle 37 and 41, respectively. These handles are formed according to the ISO standard. Instrument 36 has the standard color 40, which is a red color corresponding to the 0.25 mm tip diameter, and instrument 42 has a standard color 46, which is blue, corresponding to the 0.30 mm cutting tip diameter.

In order to clearly identify the cutting instrument 48 as an intermediate size, which intermediate size falls between the size 25 file and the size 30 file, the handle 49 is provided with a combination of colors 52, which combination 52 includes both the red color 40 and the blue color 49, on separate portions of the handle 46. Uniquely and advantageously, every dentist, dental assistant or other person trained in endodontic procedures, or root canal procedures, will immediately be able to identify this file 48 as an intermediate size because of the combination of colors on the handle. Also, they can easily determine the size as one falling between the size 25 (which is established by the red color portion) and the size 30 (which is established by the blue color portion). Based upon the combination of red and blue appearing on the handle, no confusion results. This is advantageous over designating the intermediate size with a numeric size or decimal dimension printed on the handle, because such printing is very small (these handles are typically about 1 to 1.5 cm in length and less than 0.5 cm in diameter). Thus, any imprinted number is inherently very small. Further, the files are handled with the fingertips which are as large as the handles such that the numbers can be easily covered. The intended working environment is such that such printed numbers may otherwise be obscured from view because of dental material in the operating field. Also, under use, the imprinted numbers can become worn or otherwise obliterated. In the particular embodiment shown in FIG. 2a, the combination color 52 is formed by coloring essentially one-half of the handle with one color and one-half with the another color. In this embodiment, the bottom half is provided with the ISO standard red color 40 and the top half is provided with the ISO standard blue color 46.

In the alternative embodiment of the color-coded handle 49, as shown in FIG. 2b, the reverse order of colors is depicted in which the top half is the red color 40 and the bottom half is the blue color 46. Although either color combination 52 as shown in FIG. 2a or the color combination 52 as shown in FIG. 2b may be used advantageously, the combination, as shown in FIG. 2a, is preferred for providing advantages of consistency with retroactive marking devices and methods, as will be described more fully below with reference to FIGS. 10 and 12.

FIGS. 3a and 3b show an alternative scheme for forming color combination 52 in which a color pattern, shape or design 60 is imposed upon a handle base 58. In FIG. 3a, the handle base 58 is colored with the red color 40, corresponding to the smaller standard size file, and the shape 60 is colored with the blue color 46, corresponding to the next larger standard size file. In FIG. 3b, the scheme is reversed with handle base 58 having blue color 46 corresponding to the next larger standard file size, and the shape 60 is the color red 40 corresponding to the next smaller standard file size.

In FIGS. 4a and 4b, another alternative color combination 52 is depicted in which a handle base 62 is one color corresponding to one standard size and a ring pattern is another color corresponding to another standard size one standard incremental size different from the one size, and between which standard sizes the non-standard file size is positioned. In FIG. 4a, the base handle 62 is the red color 40 such that both the top and the bottom of the file handle is red, and the central ring portion 64 is the blue color 46 corresponding to the next larger standard file size.

In FIG. 4b, the color scheme is shown reversed in which the base portion 62 is the blue color 46 corresponding to the larger standard size and the central ring portion 64 is red color 40 corresponding to the next smaller standard file size.

It will be understood by those skilled in the art that a number of other color combinations 52 may be employed according to the present invention. However, the schemes, as set forth in FIGS. 2a and 2b, 3a and 3b and 4a and 4b have been considered advantageous because of the ease of observation of the colors while using hand-held files or reamers. Either the half-and-half combination of FIGS. 2a and 2b, the imposed shape of color 60 as shown in FIGS. 3a and 3b or the interposed ring 64 as shown in FIGS. 4a and 4b will allow the user to conveniently observe the color combination 52 when grasping the handle with two fingers as is a typical method of using hand-held endodontic files or reamers.

In a further advantageous embodiment of the invention, as shown in Table II, below, a large, complete set of a plurality of standard size files or reamers with a plurality of non-standard, intermediate size files or reamers interposed between each pair of next smaller and next larger standard size files or reamers can be conveniently and advantageously accomplished using this unique color-coding scheme.

TABLE II

| | | TIP DIAMETER OF INSTRUMENT | | | |
|---|---|---|---|---|---|
| Whole Size | Half Size | ISO Standard Whole Sizes - Diameter (mm) | Non-Standard Half Sizes - Diameter (mm) | Solid Color | Combination Color |
| 10 | 12.5 | 0.10 | 0.125 | Purple | Purple/White |
| 15 | 17.5 | 0.15 | 0.175 | White | White/Yellow |
| 20 | 22.5 | 0.20 | 0.225 | Yellow | Yellow/Red |
| 25 | 27.5 | 0.25 | 0.275 | Red | Red/Blue |
| 30 | 32.5 | 0.30 | 0.325 | Blue | Blue/Green |
| 35 | 37.5 | 0.35 | 0.375 | Green | Green/Black |
| 40 | 42.5 | 0.40 | 0.425 | Black | Black/White |
| 45 | 47.5 | 0.45 | 0.475 | White | White/Yellow |
| 50 | 52.5 | 0.50 | 0.525 | Yellow | Yellow/Red |
| 55 | 57.5 | 0.55 | 0.575 | Red | Red/Blue |
| 60 | 65.0 | 0.60 | 0.65 | Blue | Blue/Green |
| 70 | 75.0 | 0.70 | 0.75 | Green | Green/Black |
| 80 | 85.0 | 0.80 | 0.85 | Black | Black/White |
| 90 | 95.0 | 0.90 | 0.95 | White | White/Yellow |
| 100 | 105.0 | 1.00 | 1.05 | Yellow | Yellow/Red |
| 110 | 115.0 | 1.10 | 1.15 | Red | Red/Blue |
| 120 | 125.0 | 1.20 | 1.25 | Blue | Blue/Green |
| 130 | 135.0 | 1.30 | 1.35 | Green | Green/Black |
| 140 | 145.0 | 1.40 | 1.45 | Black | Black/White |
| 150 | | 1.50 | | White | |

Figure 5:
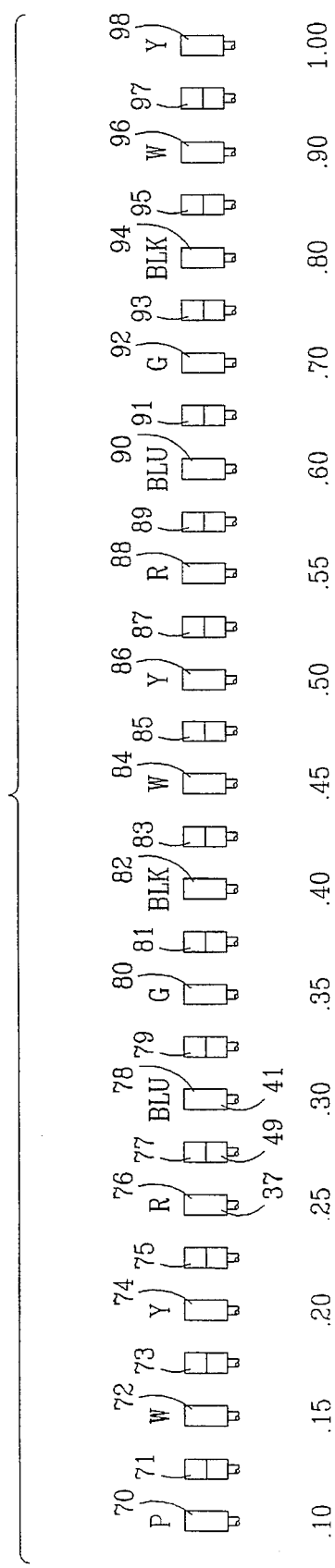
FIG. 5 is a schematic depiction of a set of endodontic cutting tools, including a plurality of standard cutting tool sizes and a plurality of intermediate, non-standard size endodontic cutting tools interposed between the next smaller and next larger sizes of said plurality of standard size cutting tools.

Thus, for example, as schematically depicted in FIG. 5, between each pair of standard smaller size and next larger standard size files, each with a standard corresponding color, there is an intermediate, non-standard size file having a combination of colors on its handle, including the color of the next smaller standard size and the color of the next larger standard size.

With reference to FIG. 5, a set of endodontic tools comprises both standard sizes ranging from 0.10 mm to 1.0 mm, which have been designated with even reference numerals 70 through 98. Also included are intermediate size files, and in particular, half-size files within the same range, each one-half of a standard increment between each standard size. The non-standard half-sizes are designated with odd reference numerals 71 through 97. It has been found that the ISO standard set provides a percentage size increase, which is inconsistent along the entire file set. Advantageously, providing half-sizes, with one each between each standard whole size, reduces the existing percentage increase between each file 70–98 at approximately one-half, also. This allows the practitioner to easily select a mid-range file size whenever the next largest file is too large and the next smaller size is too small. In any event, the amount of material to be cut is the same for each step along the set of endodontic files represented in FIG. 5. Particularly, a file increase at each step of 0.025 mm is maintained up through the blue file with a 0.60 mm working tip diameter. From that point on, the half-sizes result in a 0.5 mm size increase, which results in a cut which is one-half of the previous incremental increase of 0.10 mm. It should be noted that in the larger sizes, the strength of the file is sufficiently increased so that breakage or separation is not as great of a problem as with smaller file sizes. The increased strength of the larger files can generally withstand a larger cut depth in soft material.

It has been discovered that in normal tooth physiology, the common nerve canal has a diameter of between about 0.3 mm and 0.5 mm at its apex. Further, because of this, the normal size of available gutta percha, which is used to fill the filed root canal cavity, is about 0.4 mm. Standard methodology recommended to dental practitioners requires that a tip diameter of 0.4 mm should be obtained at a minimum, both to ensure that the bacteria-harboring soft dentin is removed completely and also to ensure that the inserted gutta percha fill the filed root canal all the way to the tip of the tooth. If the gutta percha binds before it reaches the tip, it can leave a void in which bacteria will accumulate. To a certain extent, the ISO standard is better suited for working in the most common range than some proposed constant percentage change file sets. The incremental percentage change between each whole size from 30 through 60 is less than 20%. At smaller sizes where soft dentin is most likely, the incremental percentage can be as high as 50% from one standard size 0.10 mm to 0.15 mm. Nevertheless, it has been found that the most common file or reamer which becomes separates or breaks due to a binding during an endodontic operation is in the range of 0.25 mm through 0.45 mm where the hard tooth material is encountered. For this reason, it has been found to be advantageous to provide a larger number of intermediate size files between each standard size within this range.

Figure 6:
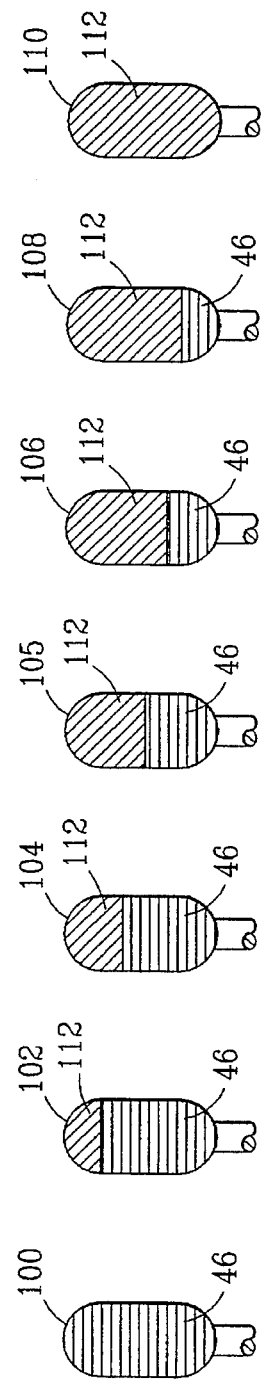
FIG. 6 is a schematic depiction of a set of a plurality of intermediate size endodontic cutting tools interposed between a first smaller standard size and a next larger standard size endodontic cutting tool in which a color combination of the handle proportionately indicates the relative size position of each of said plurality of intermediate size cutting tools between said first standard size and said second standard size cutting tool.

With reference to FIG. 6, a set of endodontic files is schematically represented in which there is a first file 100 having a first standard tip size, a second file 110 with a next larger standard tip size and a plurality of non-standard intermediate files having tip sizes falling within the range of sizes between standard file sizes 100 and 110. In the example shown in FIG. 6, there are four intermediate size files—size 102, 104, 106 and 108—each of which has an incrementally increased diameter of 0.01 mm such that where a file 100 is a blue-colored file size 1.3 mm, and file 110 is a green-colored file having a working tip diameter of 0.35 mm, then file 102 has a diameter of 0.31 mm; 104 is 0.32 mm; 106 is 0.33 mm; and 108 is 0.34 mm. As none of these files falls precisely at the half-size mark, an additional file 105 may be provided having a working tip diameter of 0.325 mm. In order to permit the practitioner to conveniently distinguish between each of these sizes within the plurality of each of the sizes, a color scheme has been devised in which the handle, having a combination of colors, is provided with a proportional amount of color according to the relative position within the 0.5 mm range between file 100 and 110. Thus, file 102 has a base having approximately 80% coverage of the blue color 46 corresponding to the next smaller standard size file. The top 20% of the handle 102 would have a green color 112. The intermediate size file 104 having a size 0.32 mm would have approximately 60% blue color 46 and 40% green color 112. File 106 would have 40% blue color 46 and 60% green color 112, while file 108 only 20% blue color 46 and 80% green color 112. The intermediate file 105, as it falls halfway between file 100 and 110 in size, would have approximately 50% green color 112 and 50% blue color 46. As with FIGS. 2b, 3b and 4b, the color scheme could be placed in reverse such that the top portion has the color of a smaller size and the bottom portion has the color of larger size.

Figure 7:
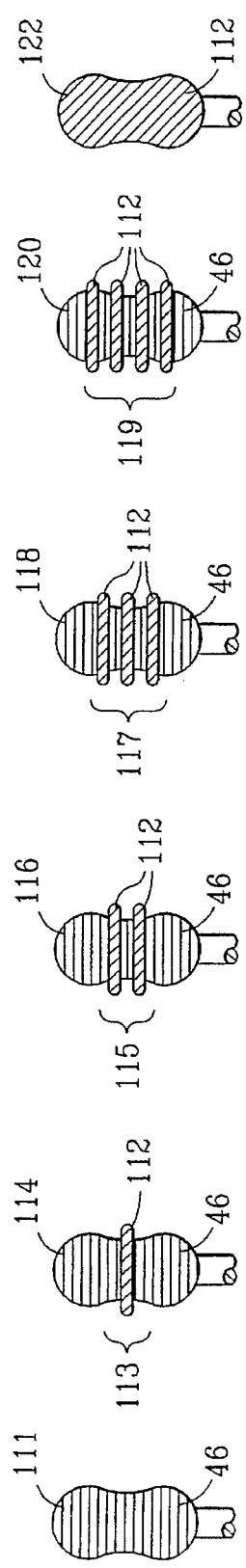
FIG. 7 depicts an alternative embodiment of a plurality of non-standard, intermediate size cutting tools and an alternative scheme for depiction of relative size with respect to the position between said first standard endodontic cutting size and the next larger standard endodontic cutting tool size.

FIG. 7 shows an alternative embodiment of a plurality of intermediate size files, again with the smaller standard size 110 shown as a blue color 46 and the larger size file 122 shown as the green color 112 corresponding to 0.30 mm and 0.35 mm, respectively. In FIG. 7, the relative size position of intermediate files 114, 116, 118 and 120 may be designated with a color ring interposed on the file handle. In the embodiment shown in FIG. 7, one ring 113 having a green color 112 is used to designate a first intermediate incremental size of a file 114 and the color 46 of the next smaller size 111 forms a base color portion. In the next larger size file 116, two rings 115 are used having the green color 112. The next larger size 118, which is 0.3 mm larger than file 111, will have three rings 117 corresponding to the green color 112; the next larger size 120 will have four rings 119 corresponding to the color 112 of the next larger ISO size file 120.

Figure 8:
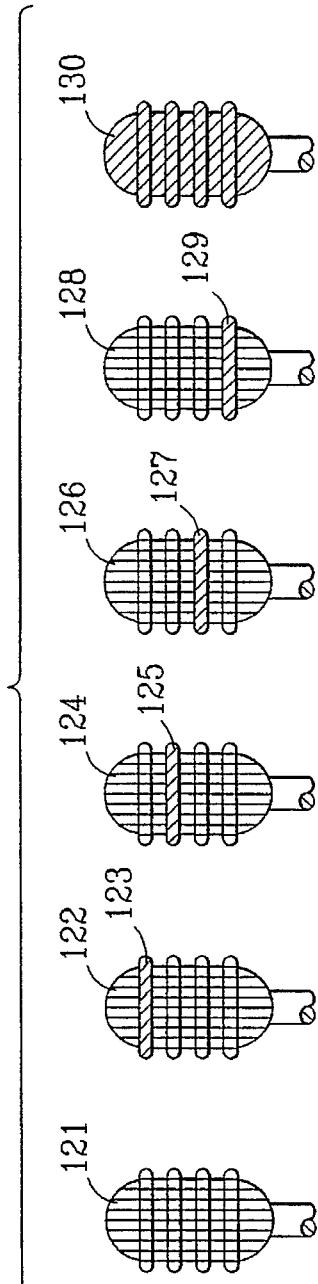
FIG. 8 is a schematic depiction of an alternative embodiment of the invention by which the relative size position between the first smaller standard size and the next larger standard size is depicted by the relative position of colored rings.

As shown in FIG. 8, another embodiment of the invention, colored rings are used for identifying sizes of an intermediate file within the size range between the smaller size 121 and the larger size 130. A colored ring 123 is positioned such that the first intermediate size file 122 has a first ring position 123 toward one end (either at the top, as shown, or at the bottom, not shown) of the file handle. The next intermediate file 124 would have an interposed color ring 125 positioned second from the end indicating that it is 0.02 mm larger than file 121. Intermediate file 126 would have a colored ring 127 in a third position away from the end, and intermediate file 128 would have a colored ring 129 in a fourth position.

Figure 9:
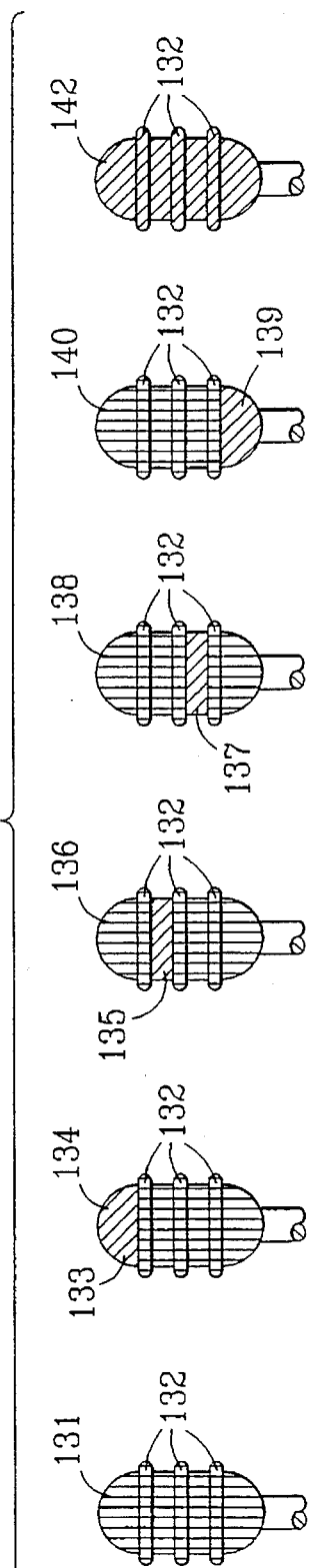
FIG. 9 is an alternative embodiment of a plurality of intermediate endodontic cutting in which the relative size is also depicted with a color-ring position.

With reference to FIG. 9, an alternative variation of the scheme of FIG. 8 is depicted in which the colored rings are interposed between raised ridge portions 132. Raised ridge portions 132 are shown on handles of standard size files 131 and 142, as well as on handles of intermediate size flies 134, 136, 138 and 140. The color coding is applied, in this alternative embodiment, such that intermediate file size 134 has a colored ring 133 at one end; intermediate file size 136 has a ring portion 133 interposed between the first and second ridges 132; intermediate size 138 has a colored ring 137 interposed between the second and third ridges 132; and intermediate file size 140 has a colored ring 139 between the bottom of the handle and the third ridge 132.

Figure 10:
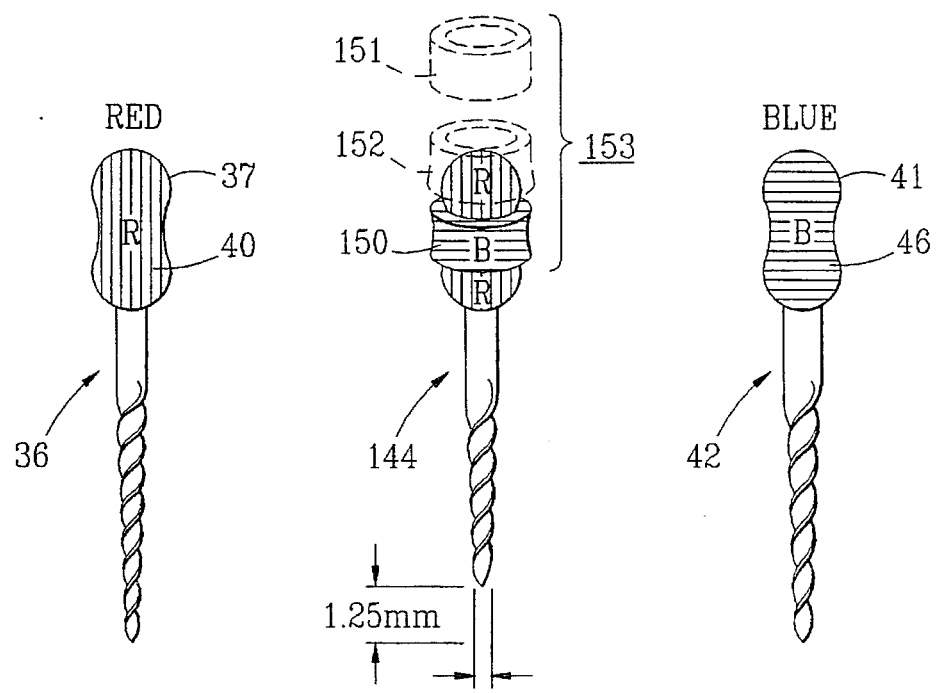
FIG. 10 is a schematic depiction of a device and method for conveniently marking intermediate endodontic cutting tools according to the color-coding system of the present invention.

With reference to FIG. 10, a set of endodontic cutting instruments with intermediate sized drilled can be converted and marked by the practitioner himself with a kit comprising resilient rings 150 which may be of a rubber or plastic material and which may be subject to adhesive bonding, welding or shrinkwrapping, or the like to ensure firm fit on the handle. In this embodiment, the next smaller file size 36 corresponding to a 0.25 mm working diameter and having a standard handle 37 with the color red 40 can be converted to an intermediate file having a working tip which is midway between the next larger standard file 42 having a handle 41 with a blue color 46. In this case, the converted tool 144 can be converted to a 0.275 mm working tip by removing 1.25 mm of the length of a next smaller size file 36. Thus, a colored ring 150 having the blue color 46 can be moved from the position 151 onto the file handle as schematically depicted with motion bracket 153.

As discussed above, in this embodiment, the base handle portion 58 has the color 40 corresponding to the next smaller handle 37. Thus, if the color code as in examples 3a and 4a are adopted or as shown in FIGS. 6 and 7 in which the base handle color is that of the next smaller standard whole size, then converted files or files converted by the user can be consistently marked with prefabricated files according to the same scheme, and in particular, the method of marking converted files as shown in FIG. 10 corresponds to a same system of marking as depicted in FIG. 4a.

Figure 11:
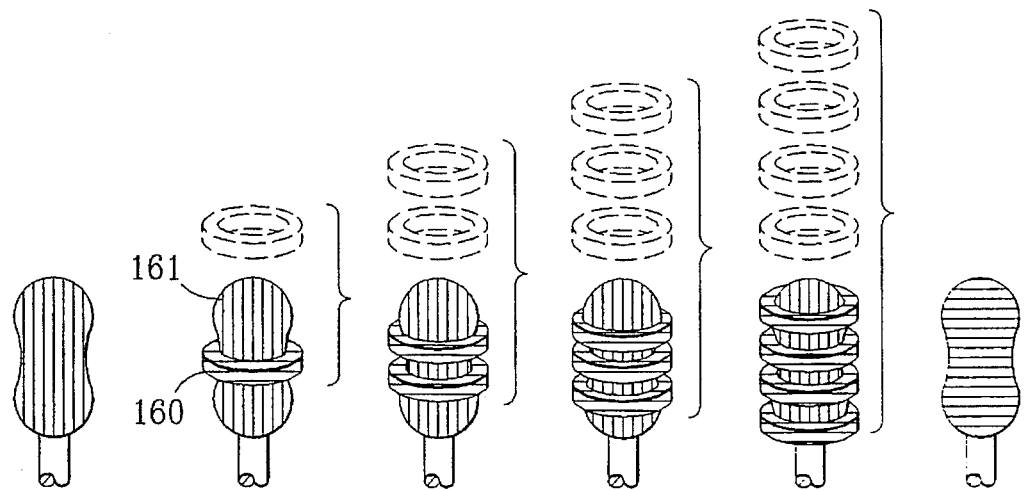
FIG. 11 is another alternative embodiment schematically depicting a method of marking a plurality of intermediate size endodontic files for designating relative size differences according to one embodiment of the present invention.

With reference to FIG. 11 where a plurality of intermediate size files are desired, intermediate files may be converted by cutting off increments of 0.5 mm from the length of the next smaller size file and by placing one colored ring 160 for each 0.5 mm cut off from the length (i.e., one ring for each increase in working tip diameter by a predetermined increment of 0.01 mm). A 0.30 mm file 100, having a blue color 46, could be converted to a 0.31 mm working tip diameter file 161 with a single colored ring 160 placed thereon. The 0.32 mm converted file 163 could be thus designated with two colored rings 160, and so on as depicted in FIG. 11, so that confusion as to the size of converted files does not result after one procedure is completed. Cleaned and sterilized converted files can be reused in subsequent procedures without risk of confusion as to the size. The dentist would immediately recognize the size increases according to the inventive color code as set forth herein. It will also be recognized that original manufacturers of intermediate size file sets could also use the same method of manufacture in which a plurality of rings are placed on an existing colored handle and secured or adhered thereto as by bonding, shrinkwrapping, plastic welding and the like, according to the method as set forth in FIGS. 10 and 11.

Figure 12:
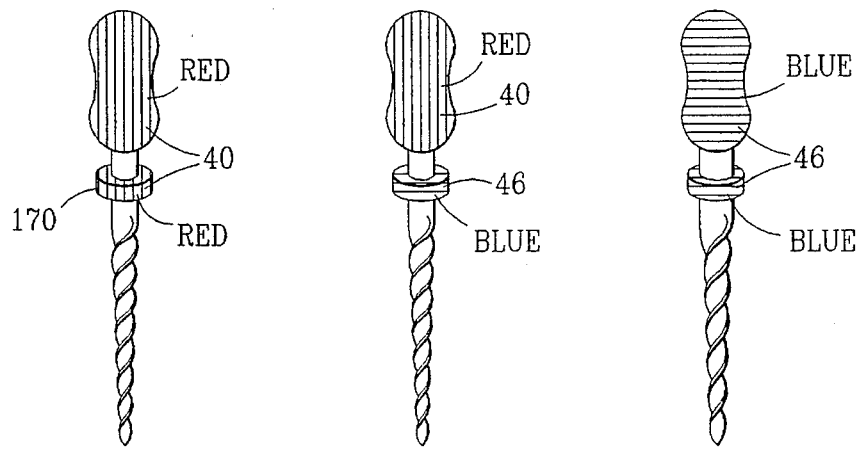
FIG. 12 is a schematic depiction of yet another alternative method of marking intermediate endodontic files in which the marking is placed on the file shank rather than on the file handle to form a color combination according to the present invention.

FIG. 12 shows another alternative embodiment in which the dentist or the manufacturer may mark midsize or intermediate size, non-standard files through the use of placing a stopper ring 170 along the shank of the intermediate size file. The stopper ring has a color corresponding to the next larger standard size. In this manner, a smaller size file 36, which is converted to a larger intermediate size file 171, could be designated with a stopper ring 170 having a color 46 corresponding to the color of the next larger standard size file 42. Where a stopper ring is used on a standard size file 36 or 42, the same color ring 40 or 46, respectively, can be used, as shown in FIG. 12.

Figure 13:
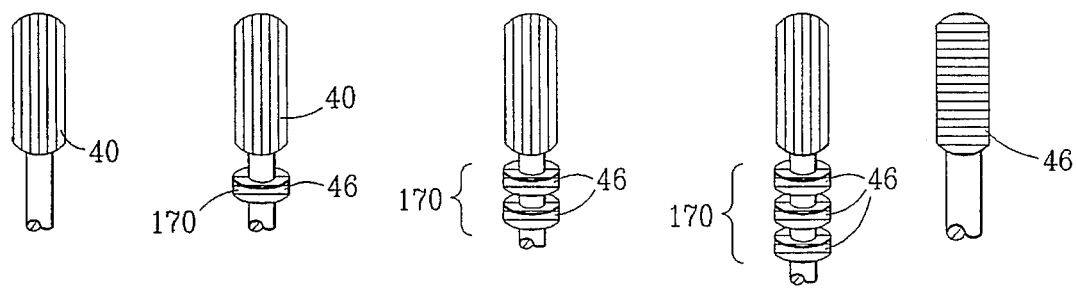
FIG. 13 is yet another alternative embodiment of a color coded marking according to the present invention.

With reference to FIG. 13, a similar use of plurality of stopper rings 170 having the color of the next larger size file could be used in order to designate converted intermediate size files which have progressively larger sizes according to the amount of the length clipped from the next smaller size file.

Figure 14:
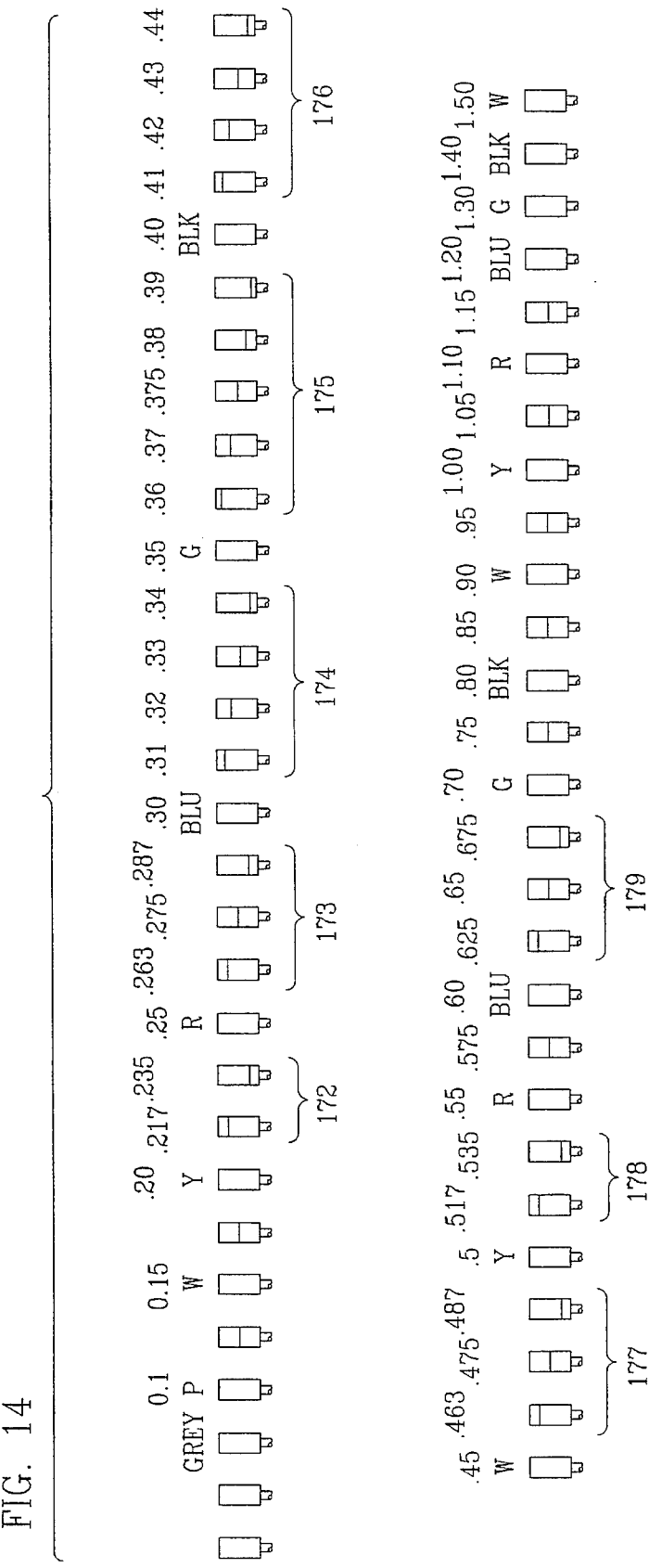
FIG. 14 is a schematic depiction of an improved complete set of endodontic tools having intermediate sizes and with a greater or lesser number of intermediate sizes positioned along the entire standard ISO size system with a greater number of intermediate files between different pairs of standard sizes, depending upon the usefulness of small size increments for working with normal human tooth physiology.

As indicated above, it has been found that certain size ranges are subject to the most use. The human tooth physiology is such that files in the size range of between 0.25 mm and 0.50 mm are most used, most subject to wear and most likely to bind such that breakage is more likely unless smaller incremental sizes are available for moving from one step to the next. For that reason, a complete system of intermediate size endodontic instruments and color coding adaptable to easily identify such sizes will be advantageous, in which system the largest number of intermediate file sizes are available precisely in the middle of the most commonly used size range. In the embodiment shown, there are two intermediate files depicted in the range 172 between 0.2 mm and 0.25 mm. Three intermediate size files 173 are depicted in the range between 0.25 mm and 0.30 mm, with the percentage size increase relationship indicated on the handle. Four intermediate size files are provided in the range 174 0.3 mm between and 0.35 mm, and color coding according to the invention indicates the relative size. For example, color coding according to a proportional marking scheme as described with reference to FIG. 6 could be used. It will be understood that in each of these ranges where the proportional marking is depicted in FIG. 14, an alternative method of marking might be used according to the invention such as described and shown in FIGS. 7, 8 or 9. The size range 175, moving from 0.35 mm standard size to 0.4 mm standard size, is preferably provided with five intermediate files. Between the range 176 of 0.40 mm standard size and 0.45 mm standard size, there are preferably four intermediate files, and in the range 177 between 0.45 mm and 0.50 mm, there are three intermediate files. The range 178, from 0.50 mm to 0.55 mm, is provided with two intermediate file sizes. Between 0.55 mm and 0.60 mm, one file size has been found to be generally sufficient. In the range 180, there is a significant incremental increase, between 0.60 mm and the next larger standard size 0.70 mm. With this significant difference, there is a plurality of about three intermediate files 180 can be advantageously used. The remainder of the larger sizes, from 0.70 mm up through about 1.2 mm, each preferably has one intermediate size file. Those standard files in the larger range from 1.2 mm to 1.5 mm are typically sufficiently strong when needed to remove as much as 0.1 mm internal diameter without significant risk of breakage.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A set of endodontic cutting instruments, each having handles and each having a different working tip diameter incrementally increasing in size from one instrument to the next, said set comprising:

(a) a first smaller standard size endodontic cutting instrument having a grasping end with a first color according to a standard color code;

(b) a second larger standard size endodontic cutting instrument having a grasping end with a second color according to said standard color code; and (c) a non-standard intermediate size endodontic instrument having a size between said first smaller standard size and said second larger standard size and having a grasping end with a color combination including a first portion having said first standard color corresponding to said first smaller standard size and a second portion having said second standard color corresponding to said second larger standard size.

2. The set of endodontic cutting instruments as in claim 1 further comprising:

(a) a plurality of additional standard size endodontic instruments, each incrementally larger than each next smaller standard size, each having an incrementally different standard size and each having a grasping end colored with one of a plurality of standard colors corresponding to each incrementally different standard size; and (b) a plurality of non-standard intermediate size endodontic instruments, each having a color-coded grasping end consisting of a combination of a color corresponding to a next smaller standard size and of another color corresponding to a next larger standard size.

3. A set of endodontic cutting instruments as in claim 1 wherein said non-standard intermediate size is a size which is about midway between said first smaller standard size and said second larger standard size and wherein said combination of colors comprises about one-half of said grasping end colored with said first color and another half of said grasping end colored with said second color.

4. A set of endodontic cutting instruments as in claim 3 wherein said one-half of said grasping end is colored with said first color at a bottom of said grasping end and said second color is at a top of said grasping end.

5. A set of endodontic cutting instruments as in claim 1 wherein said grasping end comprises a handle having said combination of colors and wherein said combination of colors of said handle of said non-standard intermediate size instrument comprises a base portion of said handle having a color corresponding to said first size and a shape imposed upon said base portion having a color corresponding to said second larger size.

6. A set of endodontic cutting instruments as in claim 5 wherein said shape of said second color is a ring around said handle.

7. A set of endodontic cutting instruments as in claim 5 wherein said combination of colors comprises a base portion of said handle having said second color and a shape imposed upon said base portion having said first color.

8. A set of endodontic cutting instruments as in claim 7 wherein said shape comprises a ring around said handle.

9. A set of endodontic cutting instruments as in claim 1 further comprising:

(a) a plurality of non-standard intermediate size instruments, each larger than said first standard size and each smaller than said second standard size and each progressively larger than the next; and (b) a handle on said grasping end of each intermediate endodontic instrument having a portion thereof colored with said first color and a second portion thereof colored with said second color, such that a relative size of said first and second portions corresponds to a relative size of each intermediate instrument with respect to each other intermediate instrument, such that a smallest intermediate instrument has a relatively largest proportion of said first color and has a relatively smallest proportion of said second color, and a largest intermediate instrument has a relatively smallest proportion of said first color and a relatively largest proportion of said second color.

10. A set of endodontic cutting instruments as in claim 1 further comprising:

(a) a plurality of non-standard intermediate size instruments, each larger than said first standard size and each smaller than said second standard size and each progressively larger than the next; and (b) a handle on said grasping end of each intermediate endodontic instrument having a base portion colored with said first color corresponding to said first color and a number of rings of said second color imposed thereamong, such that a greater number of rings is imposed on handles of relatively larger intermediate instruments.

11. A set of endodontic cutting instruments as in claim 1 further comprising:

(a) a plurality of non-standard intermediate size instruments, each larger than said first standard size and each smaller than said second standard size and each progressively larger than the next; and (b) a handle on said grasping end of each intermediate instrument having a top and a bottom and a base portion of said first color with a ring of said second color interposed therealong such that a position of said ring relative to said top and said bottom corresponds to a relative size of each progressively larger intermediate instrument relative to each other.

12. A set of endodontic instruments as in claim 1 wherein said combination color of said grasping end of said intermediate instrument comprises said first color with a ring of said second color interposed therealong.

13. A set of endodontic instruments as in claim 12 wherein said ring of said second color comprises a band having said first color sized for slip fit engagement over said grasping end, such that instruments originally having said first standard size which are subsequently converted to a larger intermediate diameter can be conveniently designated as a non-standard half size by engaging said second colored ring thereover.

14. A set of endodontic instruments as in claim 1 wherein said instruments are endodontic files.

15. A set of endodontic instruments as in claim 1 wherein said instruments are endodontic reamers.

16. A set of endodontic instruments comprising:

(a) a pair of standard size elongated endodontic cutting instruments, one larger than the other, by a standard incremental difference and each having a different visibly displayed standard color corresponding to said standard size according to a standardized color code;

(b) a non-standard intermediate size endodontic cutting instrument smaller than said one larger standard size endodontic instrument and larger than said other smaller standard size endodontic instrument and having a visibly displayed combination of colors, including said standard color corresponding to said one larger standard size and also including said standard color corresponding to said other smaller standard size.

17. The set of endodontic instruments as in claim 16 further comprising:

(a) a plurality of additional standard size instruments, each incrementally larger than the next by a standard increment and each having a grasping end colored with a standard color different from each next large and each next smaller standard size instrument and corresponding to each standard size according to an existing standardized color code; and (b) a plurality of non-standard intermediate size endodontic instruments, each having a grasping end colored with a combination of said color corresponding to the next smaller standard size and of said color corresponding to the next larger standard size.

18. A set of endodontic files as in claim 16 wherein said non-standard intermediate size is a size which is about midway between the next smaller standard size and said next larger standard size and wherein said visibly displayed combination of colors comprises about one-half of said grasping end colored with said color corresponding to said next smaller or standard size about another half of said grasping end colored with said a color corresponding to said next larger standard size.

19. A system of color coding sets of endodontic cutting instruments having different sizes comprising:

(a) a first standard solid color corresponding to a first standard size endodontic cutting instrument;

(b) a second standard solid color corresponding to a second standard size endodontic cutting instrument, which is a predetermined standard increase in size over said first standard size; and (c) a combination of said standard first solid color and said second standard solid color corresponding to a non-standard size endodontic cutting instrument which has a size between said first standard size and said second standard size endodontic cutting instrument.

20. The system of color-coding endodontic instruments as in claim 19 further comprising:

(a) a plurality of additional standard solid color files, each incrementally larger than the next by a standard increment and each having a grasping end colored with a standard solid color corresponding to each of a plurality of additional standard size endodontic cutting instruments; and (b) a plurality of non-standard intermediate size endodontic files, each having a color-coded grasping end consisting of combinations of two solid colors, one color corresponding to a color of a next smaller standard size and of another color corresponding to a color of a next larger standard size.

21. A method of color coding sets of endodontic instruments, which sets include at least two standard size instruments and non-standard size instruments, comprising the steps of:

(a) determining which of said at least two standard sizes is next smaller and which is next larger than an intermediate instrument; and (b) marking said intermediate size instruments with a combination of colors, including a color corresponding to a standard color for said next smaller standard size and another color corresponding to said next larger standard size.

22. The method of claim 21 wherein the step of marking said intermediate size instrument with a combination of colors further comprises forming half of a grasping end with a color corresponding to next smaller size and forming another half of said grasping end with a color corresponding to said next larger size.

23. A method of color coding sets of endodontic instruments as in claim 21 wherein said step of marking said intermediate size instruments comprises forming a handle having a base portion with a color corresponding to said next smaller size and forming a shape of color on said base portion having a color corresponding a standard color for said next larger size.

24. A method of color coding sets of endodontic instruments as in claim 21 wherein said step of marking said intermediate size instruments comprises forming a handle for said intermediate size instrument of a color corresponding to said next smaller size and placing a ring of color corresponding to the next larger size around said handle.

25. An improved set of endodontic instruments comprising:

(a) a first subset of endodontic instruments having standard size instrument over a range of instrument sizes, each instrument a predetermined incremental size larger than the next and each instrument having a color-coded grasping end corresponding to the ISO standard colors for each size standard instrument within said range of instrument sizes;

(b) a subset of intermediate size instruments, each having a different non-standard size such that each different non-standard size is larger than one of said standard ISO size instruments and smaller than the next larger ISO standard instrument within said range and wherein each intermediate size instrument has a grasping end with a combination of two colors, including a first color corresponding to a standard color of said ISO standard colors for said one ISO standard size instrument and a second color corresponding to a next of said standard ISO colors for said next larger ISO standard size instrument.

26. An improved endodontic instrument set as in claim 25 wherein said range of instrument sizes include an ISO standard instrument having a working tip diameter of 0.15 mm and an ISO standard instrument having a working tip diameter of 0.60 mm, and wherein there is a plurality of intermediate size instruments between each of said ISO standard size instrument in the range between 0.25 mm and 0.45 mm.

* * * * *